(12) United States Patent
Singh et al.

(10) Patent No.: US 9,896,425 B2
(45) Date of Patent: Feb. 20, 2018

(54) PROCESS FOR PURIFYING AN ACID COMPOSITION COMPRISING 2-FORMYL-FURAN-5-CARBOXYLIC ACID AND 2,5-FURANDICARBOXYLIC ACID

(71) Applicant: FURANIX TECHNOLOGIES B.V., Amsterdam (NL)

(72) Inventors: Jagdeep Singh, Amsterdam (NL); Benjamin McKay, Amsterdam (NL); Bing Wang, Amsterdam (NL); Matheus Adrianus Dam, Amsterdam (NL); Gerardus Johannes Maria Gruter, Amsterdam (NL); Ana Sofia Vagueiro De Sousa Dias, Amsterdam (NL)

(73) Assignee: SYNVINA C.V., Amsterdam (NL)

( * ) Notice: Subject to any disclaimer, the term of this patent is extended or adjusted under 35 U.S.C. 154(b) by 28 days.

(21) Appl. No.: 14/914,972

(22) PCT Filed: Aug. 29, 2014

(86) PCT No.: PCT/NL2014/050589
§ 371 (c)(1),
(2) Date: Feb. 26, 2016

(87) PCT Pub. No.: WO2015/030590
PCT Pub. Date: Mar. 5, 2015

(65) Prior Publication Data
US 2016/0207898 A1    Jul. 21, 2016

(30) Foreign Application Priority Data

Aug. 30, 2013 (NL) .................................... 2011362

(51) Int. Cl.
C07D 307/68       (2006.01)
C07B 63/02        (2006.01)

(52) U.S. Cl.
CPC ............ *C07D 307/68* (2013.01); *C07B 63/02* (2013.01)

(58) Field of Classification Search
CPC .................................................. C07D 307/68
See application file for complete search history.

(56) References Cited

U.S. PATENT DOCUMENTS

| | | |
|---|---|---|
| 2007/0232815 A1 | 10/2007 | Miura et al. |
| 2012/0302768 A1 | 11/2012 | Janka et al. |
| 2013/0131376 A1 | 5/2013 | Marenco et al. |
| 2013/0331491 A1 | 12/2013 | Becker et al. |
| 2014/0024754 A1 | 1/2014 | Becker et al. |

FOREIGN PATENT DOCUMENTS

| | | |
|---|---|---|
| DE | 10 2011 004 676 A1 | 8/2012 |
| DE | 10 2011 004 677 A1 | 8/2012 |
| EP | 2 481 733 A1 | 8/2012 |
| WO | WO 2011/043660 A2 | 4/2011 |
| WO | WO 2011/043661 A1 | 4/2011 |
| WO | WO 2012/017052 A1 | 2/2012 |
| WO | WO 2012/161968 A1 | 11/2012 |
| WO | WO 2012/161970 A2 | 11/2012 |
| WO | WO 2012/161971 A2 | 11/2012 |
| WO | WO 2012/161972 A1 | 11/2012 |
| WO | WO 2012/161973 A1 | 11/2012 |
| WO | WO 2013/191940 A1 | 12/2013 |
| WO | WO 2013/191942 A1 | 12/2013 |
| WO | WO 2013/191943 A1 | 12/2013 |
| WO | WO 2014/035240 A1 | 3/2014 |
| WO | WO 2014/099438 A2 | 6/2014 |
| WO | WO 2014/163500 A1 | 10/2014 |

OTHER PUBLICATIONS

University of Illinois. "How to name organic compounds using the IUPAC rules." © Aug. 10, 2011. Available from: < http://web.archive.org/web/20110810190326/http://www.chem.uiuc.edu/GenChemReferences/nomenclature_rules.html >.*

* cited by examiner

*Primary Examiner* — Noble Jarrell
*Assistant Examiner* — John S Kenyon
(74) *Attorney, Agent, or Firm* — Birch, Stewart, Kolasch & Birch, LLP

(57) ABSTRACT

An acid composition comprising 2-formyl-furan-5-carboxylic acid and 2,5-furandicarboxylic acid is purified in a process which comprises; contacting the acid composition with an alcohol to obtain an esterified composition; and separating the ester of 2-formyl-furan-5-carboxylic acid from the esterified composition to obtain a purified esterified product; and contacting the purified esterified composition with water for saponification or hydrolysis, to obtain a product composition, comprising 2,5-furandicarboxylic acid and a reduced amount of 2-formyl-furan-5-carboxylic acid.

21 Claims, 1 Drawing Sheet

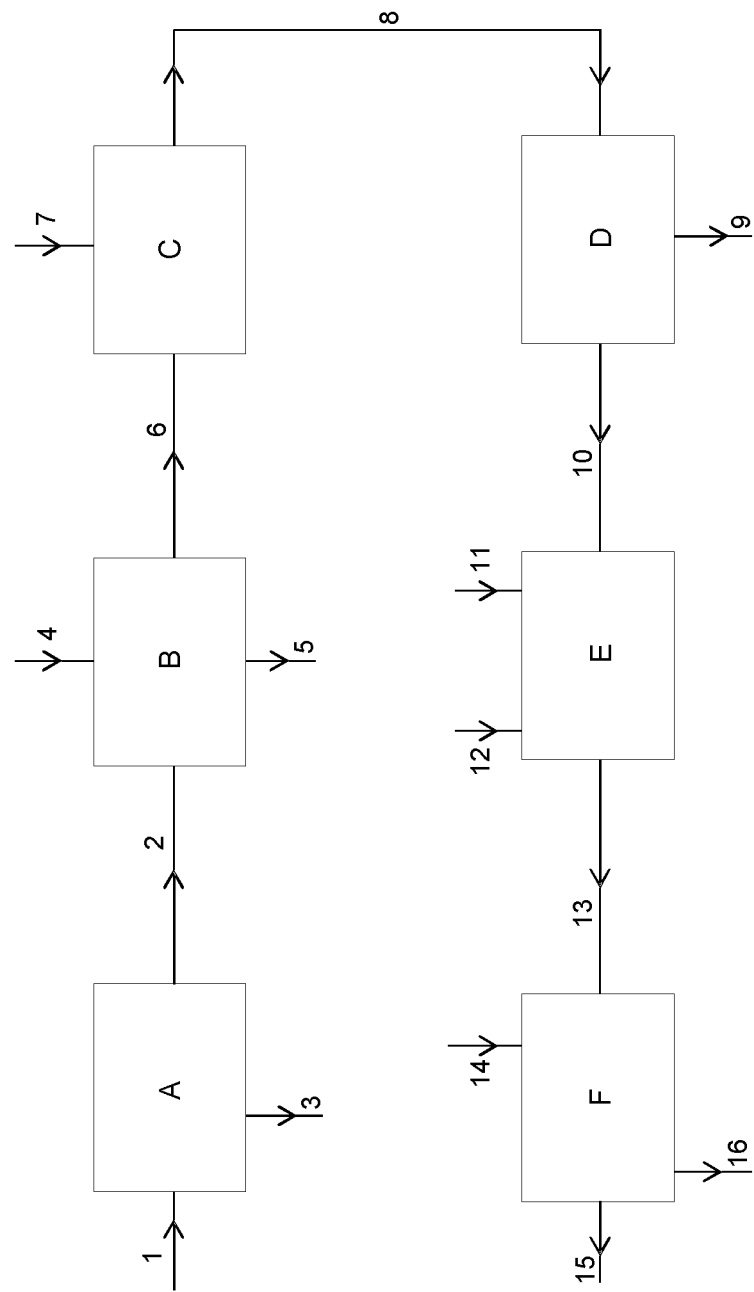

PROCESS FOR PURIFYING AN ACID COMPOSITION COMPRISING 2-FORMYL-FURAN-5-CARBOXYLIC ACID AND 2,5-FURANDICARBOXYLIC ACID

The present invention relates to a process for purifying an acid composition comprising 2-formyl-furan-5-carboxylic acid (FFCA) and 2,5-furandicarboxylic acid (FDCA).

US 2012/0302768 discloses an oxidation process to produce a crude and/or a purified carboxylic acid product. The product is a carboxylic acid composition comprising 2,5-furan-dicarboxylic acid. It has been obtained in a process comprising the oxidation of a feedstock containing 5-hydroxymethylfurfural in the presence of oxygen, of a saturated organic acid solvent having 2 to 6 carbon atoms, and of a catalyst system. The feedstock may also comprise ethers of 5-hydroxymethylfurfural, such as 5-ethoxymethylfurfural. It is described that the oxidation reaction leads to the formation of a mixture of 2,5-furan-dicarboxylic acid, 2-formyl-furan-5-carboxylic acid and, optionally, some other furan derivatives, such as alkyl esters of 2-formyl-furan-5-carboxylic acid. The amount of 2-formyl-furan-5-carboxylic acid may range from 0.1 wt % to about 4 wt %. After the oxidation the crude product obtained is washed with the organic acid solvent, e.g. acetic acid, and water. Although it is stated that purified 2,5-furan-dicarboxylic acid can be obtained, it was found that also the purified product still contained an amount of 2-formyl-furan-5-carboxylic acid. It is acknowledged in US 2012/0302768 that significant concentrations of mono-functional molecules like 2-formyl-furan-5-carboxylic acid in the 2,5-furan-dicarboxylic acid product are particularly detrimental to polymerization processes as they may act as chain terminators during a polyester condensation reaction.

The present inventors have found that further washing does not yield any purer product. It is believed that 2-formyl-furan-5-carboxylic acid is included in the crystals of 2,5-furan-dicarboxylic acid whereby the purification by washing becomes unfeasible.

Therefore, there is a need for a process that enables the reduction of the amount of 2-formyl-furan-5-carboxylic acid in a carboxylic acid composition that comprises 2,5-furan-dicarboxylic acid. It has now been found that the amount of 2-formyl-furan-5-carboxylic acid in such compositions can be reduced considerably by esterification of the composition and subsequent separation of the esterified product thus obtained.

Accordingly, the present invention provides a process for purifying an acid composition comprising 2-formyl-furan-5-carboxylic acid and 2,5-furandicarboxylic acid, which process comprises;
contacting the acid composition with an alcohol to obtain an esterified composition; separating the ester of 2-formyl-furan-5-carboxylic acid from the esterified composition to obtain a purified esterified product; and
contacting the purified esterified composition with water for saponification or hydrolysis, to obtain a product composition, comprising 2,5-furandicarboxylic acid and a reduced amount of 2-formyl-furan-5-carboxylic acid.

The process according to the invention employs the surprising fact that the esterified composition enables an easier separation of the ester compounds of 2-formyl-furan-5-carboxylic acid from the esterified product than the corresponding acid from the acid composition. It is believed that molecules of the ester of 2-formyl-furan-5-carboxylic acid are not or at least to a lesser extent incorporated into the crystals of the diester of 2,5-furan-dicarboxylic acid. The product of the process is a composition that comprises an increased content of 2,5-furan-dicarboxylic acid compounds, in comparison with the content thereof in the acid composition. By 2,5-furan-dicarboxylic acid compounds is understood the 2,5-furan-dicarboxylic acid but also the mono- and diester of 2,5-furan-dicarboxylic acid.

Although recrystallization of the starting material, i.e. the acid composition, may be used to obtain a purer product, the inclusion of 2-formyl-furan-5-carboxylic acid in crystals of 2,5-furan-dicarboxylic acid have the drawback that purer product can only be obtained at a considerable loss of yield. It is surprising that the esterification allows a simpler and more efficient purification method, since the mixture after esterification tends to be more complex in that not only the mono- and diester of 2,5-furan-dicarboxylic acid will be present in this mixture, but also small amounts of 2,5-furan-dicarboxylic acid. In spite of the complexity of this mixture, the separation of the ester of 2-formyl-furan-5-carboxylic acid is simplified, which results in a pure product at an increased yield, compared to e.g. recrystallization of the acid composition.

The FIGURE shows a simplified flow scheme for an embodiment of the process according to the present invention.

The acid composition that is used as the feedstock for the process according to the present invention can be produced in a way similar to the one described in US 2012/0302768. That means that the acid composition can be produced by the oxidation of 5-hydroxymethylfurfural. Also, as described in US 2012/0302768 the starting material may be an ether of 5-hydroxymethylfurfural, or an ester, such as 5-acetoxymethylfurfural. Preferably, the acid composition originates from the oxidation of 5-alkoxymethylfurfural, 5-hydroxymethylfurfural or a mixture thereof. When the acid composition originates from the oxidation of a 5-alkoxymethylfurfural-containing feedstock, the oxidized product may comprise FDCA and FFCA, but also the mono- and the diester of FDCA and the alkyl ester of FFCA. The process according to the present invention provides an elegant procedure of purifying the complex mixture into pure FDCA.

The oxidation of 5-hydroxymethylfurfural or derivatives thereof may be conducted as described in US 2012/0302768. A suitable manner for oxidizing 5-alkoxymethylfurfural has also been described in WO 2011/043660. The conditions according to the latter application include a reaction temperature of 60 to 220° C., preferably from 100 to 210° C., more preferably from 150 to 200° C., most preferably from 160 to 190° C., and a pressure from 5 to 100 bar, preferably from 10 to 80 bar. The catalysts that may be used in this oxidation reaction are similar to those described in US 2012/0302768. They suitably include cobalt and manganese. In addition, they contain a bromide source. The molar ratios of cobalt to manganese (Co/Mn) are typically 1/1000-100/1, preferably 1/100-10/1 and more preferably 1/10-4/1. Molar ratios of bromide to metals (e.g. Br/(Co+Mn)) are typically 0.001-5.00, preferably 0.01-2.00 and more preferably 0.1-0.9. The oxygen is suitably provided by air, although oxygen-enriched air or oxygen depleted air may also be used. It is surprising that the main product of the oxidation according to WO 2011/043660 yields the furan-2,5-dicarboxylic acid as the main product rather than the monoester thereof.

As shown in US 2012/0302768 the acid composition obtained by such oxidation reactions may contain up to a significant level of 2-formyl-furan-5-carboxylic acid. When the starting material for the oxidation reaction comprises an ether the product thereof may also comprise an ester of 2-formyl-furan-5-carboxylic acid. However, the main by-product is the acid compound, also in the case of the oxidation of an ether. The amount of 2-formyl-furan-carboxylic acid in the acid composition may be in the same order of magnitude as described in US 2012/0302768. Typically, the acid composition comprises from 0.1 to 4.0% wt of 2-formyl-furan-5-carboxylic acid, based on the weight of the acid composition. The composition may have been washed, as described in US 2012/0302768. It is however observed that by such washing step no significant reduction of the content of 2-formyl-furan-5-carboxylic acid takes place. Suitable washing liquids include acetic acid, water, and mixtures thereof.

The process according to the present invention comprises a step of contacting the acid composition with an alcohol. The alcohol may be selected from a wide range of alcoholic compounds. Such alcoholic compounds include mono-alcohols, but also polyols, such as ethylene glycol, propylene glycol, glycerol, pentaerythritol and the like. Preferably, the alcohol has from 1 to 16, more preferably from 1 to 8 carbon atoms. The alcohol is suitably a mono-alcohol. Such alcohols include linear and branched aliphatic, cycloaliphatic and aromatic alcohols. The alcohol is suitably an alkanol having 1 to 16, more preferably from 1 to 8 carbon atoms. Such alcohols can be easily used in the esterification reaction, and provide a suitably different behaviour of the resulting esters to allow the facilitation of the separation of the resulting esters. The alkanols may be linear or branched, and include n-propanol, isopropanol, n-butanol, iso-butanol, tert-butanol, ethylhexyl alcohol, n-octanol and the like. Most preferred are methanol and ethanol.

The alcohol can be present in a wide range of proportions compared to the acid functions in the acid composition. Since esterification is an equilibrium reaction, it is preferred to use a molar excess of alcohol vis-à-vis the acid functions in the acid composition. Suitably, the alcohol is present in a molar excess of the acid composition, the molar ratio between alcohol and the acid composition preferably being from 2:1 to 100:1. It has surprisingly been found that 2-formyl-furan-5-carboxylic acid can be easily esterified and that the equilibrium for this esterification is far towards the ester side. Therefore, the esterification to the ester of 2-formyl-furan-5-carboxylic acid can be achieved virtually quantitatively. It is not necessary to remove water that is generated by the esterification reaction. If such water removal is considered it is feasible to use dry molecular sieves, or other conventional desiccants like anhydrous calcium chloride, sodium sulfate, calcium sulfate, magnesium sulfate and mixtures thereof. The desiccant may be added to the mixture the acid composition and the alcohol and any water that is generated may be adsorbed by the desiccant. It is also possible to use a soxhlet apparatus or a similar equipment, wherein the alcohol, containing some water, is refluxed and the liquid is passed along the desiccant that adsorbs any water that is incorporated in the reflux stream. Another method for removing water may be carried out in a similar way as described in EP 2481733, i.e. by using a purge gas. Therefore, a purge gas may be present in the process according to the invention; the purge gas is preferably an inert gas, i.e. a gas that is non-reactive with the educts, products, intermediates and apparatus of the process according to the present invention. Useful inert gases are nitrogen, carbon dioxide, and all noble gases, such as neon and argon and mixtures thereof. Particularly preferred is a purge gas that is or comprises nitrogen gas. Thus, the water may be removed from the purge gas after exit from the reaction chamber, such as by condensation or adsorption.

The purge gas is preferably recycled. As indicated before, water removal is not required. It may even be possible to add diluents to the mixture of the acid composition and the alcohol. Such diluents may comprise water. Other diluents may comprise organic solvents, such as sulfoxides, e.g. dimethylsulfoxide, and ketones, e.g. acetone.

To enhance the esterification rate the contact of the acid composition with the alcohol may suitably be conducted in the presence of an esterification catalyst. A suitable esterification catalyst is an acid catalyst. Many acid catalysts are suitable for catalysing the esterification reaction of the present invention. Suitable catalysts include mineral inorganic acids, organic Brønsted acids, Lewis acids, acid ion exchange resins and acid zeolites. The catalyst may be homogeneous, but also heterogeneous, including the catalysts described in EP 2481733. Examples of inorganic mineral acids include hydrochloric acid, sulphuric acid, phosphoric acid and nitric acid. Suitable organic Brønsted acids comprise methane sulphonic acid, toluene sulphonic acid and trichloroacetic acid. Suitable Lewis acids include boron trifluoride and aluminium trichloride. Preferably, the acid catalyst is selected from the group consisting of mineral inorganic acids, zeolites, ion exchange resins and mixtures thereof. Examples of the mineral inorganic acids are those mentioned above. Examples of ion exchange resins are divinylbenzene/styrene polymer resins containing sulphonic groups. Suitable zeolites are crystalline aluminosilicates and aluminophosphates. Examples of suitable zeolites include zeolite X, zeolite Y, zeolite beta, ferrierite, mordenite, chabazite, ZSM-5, ZSM-11, ZSM-23, SAPO-5, SAPO-11 and SAPO-34. Preferably the zeolites are in their H-form, indicating that they have been subjected to ion exchange to replace metal cations, such as alkali metal ions, by protons, thereby increasing their acidity. Examples of suitable ion exchange resins include sulphonated polymer resins, e.g. sulphonated styrene-divinylbenzene copolymers, such as the Amberlyst resins (ex Rohm and Haas), and sulphonated tetrafluoroethylene based fluoropolymer-copolymers, such as the Nafion resins (ex DuPont). A particularly suitable ion exchange resin is Amberlyst 70, a styrene-divinylbenzene copolymer containing sulphonic acid groups and which is reported to be halogenated and is stated to exhibit a high thermal stability.

Heterogeneous catalysts are suitably used in continuous processes. In such processes they may get deactivated, e.g. by impurities in the reaction mixtures or by thermal degradation. It was found that especially the ion exchange resins can be easily regenerated by flushing a solution of sulphuric acid in an alcohol, in particular methanol or ethanol, over the deactivated catalyst, thereby restoring the acid sites in the ion exchange resin.

The esterification reaction may be conducted in a batch or continuous reactor. In a batch reactor the reaction mixture may be maintained substantially until equilibrium has been reached. Preferably, the esterification is carried out in a continuous reactor. Suitable reactors include a continuous stirred tank reactor and a plug flow reactor. Advantageously, the esterification is carried out in a reactive stripping column. In such a column, a liquid containing the acid composition, e.g. a solution of the acid composition in a $C_1$-$C_4$-alcohol, such as methanol or ethanol, is passed over a bed of heterogeneous catalyst, and countercurrently a gas is passed over the catalyst. The gas may comprise an inert gas, such as nitrogen, noble gases or carbon dioxide. In such a case, the alcohol may be passed along with the acid composition in the liquid phase over the catalyst. However, when the alcohol is vaporous at the prevailing conditions, it is preferred to use the alcohol vapor. The acid-containing liquid is usually passed downwards over the catalyst bed and the gas is usually passed upwards. The gas will entrain at least part of the water formed during the esterification, thereby influencing the degree of ester formation. The use of reactive stripping is particularly advantageous in the present process since the removal of water will reduce the amount of monoester formed whilst enhancing the formation of the diester. Hence, the esterified composition obtained in the process of the present invention then comprises the ester of 2-formyl-furan-5-carboxylic acid and the diester of 2,5-furan-dicarboxylic acid as main products. Separation between these two compounds is relatively easy.

Since the mixture of the acid composition and the alcohol already contains acid compounds, viz. 2-formyl-furan-5-carboxylic acid and 2,5-furan-dicarboxylic acid, the mixture already is acidic. Therefore, it is not required that an additional acidic esterification catalyst is added to the mixture. It has been found that a satisfactory degree of esterification of especially 2-formyl-5-carboxylic acid is obtained when the esterification according to the invention is carried out in the absence of an esterification catalyst so that the esterification is auto-catalyzed. By esterification catalyst is meant any catalyst other than any one of the acids in the acid composition. It is advantageous to conduct the esterification by autocatalysis, since in this way no other acid components are introduced into the reaction mixture. That may render any subsequent neutralisation and/or purification step superfluous.

The esterification reaction may be carried out in a wide range of conditions as to temperature and pressure. The temperature may be as low as the reflux temperature of the alcohol with which the acid composition is contacted. That would mean that a suitable minimum temperature is in the order of 65° C. The pressure can be atmospheric. In order to increase the reaction rate the temperature and pressure are suitably elevated. Suitably, the acid composition is contacted with an alcohol at a temperature of 100 to 250° C., preferably from 120 to 180° C. The pressure is suitably selected such that the alcohol is in the liquid phase at the prevailing temperature. Typically that means that the minimum pressure is suitably at least the vapour pressure of the alcohol. The maximum pressure is determined by practical considerations. Typically this implies that the pressure may vary from 1 to 100 bar, preferably from 1 to 50 bar.

Due to the different properties of the ester compounds of 2-formyl-furan-5-carboxylic acid on the one hand and 2,5-furan-dicarboxylic acid on the other hand, it is possible to separate the 2-formyl-furan-5-carboxylate ester from the esterified product. Suitable separation technologies include dissolution, distillation and crystallisation. Thanks to the difference in solubilities, it is possible to wash the esterified product with a washing liquid that provides a higher solubility for the 2-formyl-furan-5-carboxylate ester than for the mono- and/or diester of 2,5-furan-dicarboxylic acid. A suitable washing liquid could be an alcohol, such as methanol. The use of acids, such as acetic acid, is also feasible. The alcohol and/or the acid can further be mixed with water. Such a washing treatment is especially suitable when the esterified product is obtained as a solid product and can be subjected to a washing step. Suitably the esterified composition is subjected to crystallization and/or distillation.

A very suitable separation technique is crystallization. Such is very convenient when the esterification is conducted at elevated temperature and in solution. By cooling the reaction mixture wherein the contact between the acid composition and the alcohol has taken place, the esterified composition tends to crystallise. Due to the difference in solubilities, the crystallised product contains a reduced content of 2-formyl-furan-5-carboxylate-group containing compounds. The solid crystallised material consists mainly of furan-2,5-dicarboxylic acid and the mono- and diester thereof. Since this represents a very convenient method for separating the purified esterified product obtained in the process according to the invention, the process is preferably conducted such that the esterified composition is allowed to crystallize by cooling it to a temperature of −30 to 40° C., preferably −10 to 30° C.

Another suitable crystallization technique is melt crystallization. Melt crystallization is considered suitable when two or more substances of comparable melting points are to be separated by some degree of cooling. The degree of completeness of such separations may depend on the phase equilibrium relations. When the crystals must be refined to remove occluded substances, the recovered material may leave the process in molten form. Subsequently, it may be solidified as flakes or sprayed granules. Melt crystallization (sometimes referred to as extractive crystallization) is based on the principle that when an impure molten material is cooled to its freezing point and further heat is removed, some of the material will solidify. In most cases the solidified material is pure. Impurities tend to concentrate in the melt. Purified product is recovered by separating the solidified material from the melt and re-melting it. The melt crystallization may be carried out in static, falling film and suspension crystallization equipment, as is known in the art.

Another separation technique that can suitably be applied is distillation. Generally, the alcohol will be first removed by distillation; then the esterified product will be subjected to fractionation. Typically the ester of 2-formyl-furan-5-carboxylic acid, the diester and monoester of 2,5-furan-dicarboxylic acid and any remaining 2,5-furan-dicarboxylic acid will be fractionated in one or more fractionation columns. The distillation will generally be conducted in vacuo in order to allow a temperature that is practically low. The skilled person will be able to select the appropriate distillation conditions, including reflux ratio, use of reboiler etc. It has been found that the compounds are not thermally affected if the temperature remains below 200° C., preferably below 180° C. Suitable distillation conditions therefore comprise a bottom column temperature in the range of 150 to 200° C., preferably of 150 to 180° C., and a top column temperature in the range of 120 to 150° C., and a column pressure in the range of 1 to 30 mbar.

The purified esterified product obtained in the process of the present invention has a reduced content of 2-formyl-furan-5-carboxylic acid ester. The amount of the ester of 2-formyl-furan-5-carboxylic acid may be dependent on the severity with which the ester has been separated from the esterified product. The separation may suitably have been carried out by crystallization and/or distillation. The skilled person will realize that by means of repeating the separation steps, e.g. recrystallizing the purified esterified product one or more times, the purity of the resulting product can be further increased. Typically the purified esterified product has a content of the ester of 2-formyl-furan-5-carboxylic acid in the range of 0 to 200 ppmw. By repeated distillation and/or recrystallization the amount of ester of 2-formyl-furan-5-carboxylic acid may be reduced to between 0 and 100 ppmw, suitably from 0 to 50 ppmw.

According to the present invention the purified esterified composition is contacted with water for hydrolysis or saponification, to obtain a product composition, comprising 2,5-furan-dicarboxylic acid and a reduced amount of 2-formyl-furan-5-carboxylic acid in comparison to the acid composition that was used as starting material in the process of the present invention.

By saponification is understood the base catalyzed hydrolysis of an ester whereby an alcohol and salt of the acid is formed. The process usually involves the reaction of an aqueous alkali metal base, such as NaOH or KOH, with an ester to form an alkali metal salt. The alkali metal base is usually present in at least a stoichiometric amount to allow for the formation of the salt.

Hydrolysis of esters is well known in the art. The reaction comprises contacting the ester in question with water. Suitably, the water has been acidified or rendered alkaline. Acids and bases tend to catalyse the hydrolysis of the ester. Therefore, the purified esterified product is suitably contacted with water in the presence of a hydrolysis catalyst. The catalyst can be selected from a wide range of acid or alkaline compounds. It is most convenient to apply inorganic acids, such as sulphuric acid, hydrochloric acid, nitric acid and the like. Also the use of Lewis acids, such as aluminium trichloride, may be used. Suitable alkaline catalysts include the alkali metal hydroxides, such as sodium or potassium hydroxide, but salts of weak organic acids may also be used. Salts of formic acid, acetic acid, propionic acid or butyric acid are suitable examples. The cation can be any metal ion, such as an alkali metal ion or alkaline earth metal ion. Other metal salts of such weak organic acids, such as the zinc salts, may also be used. It is advantageous if the salts are soluble in water. The skilled person will realize that the nature of the hydrolysis catalyst is not of critical importance.

Although the hydrolysis catalyst may increase the reaction rate of the hydrolysis it may have the drawback that by introducing the catalyst an extraneous compound is added that may contaminate the resulting acids. Therefore, the hydrolysis of the purified esterified composition, i.e. the contact of the purified esterified composition with water, is suitably carried out in the absence of a hydrolysis catalyst. It appeared that the conversion of the esters in the purified esterified composition is running smoothly also without an additional hydrolysis catalyst. Since the risk of contamination is being avoided by carrying out the hydrolysis in the absence of an additional hydrolysis catalyst, such a process is preferred.

Hydrolysis conditions are well known in the art. It is conventional to heat the ester in water in the presence or absence of an acid or a base. A suitable temperature range may be from 100 to 200° C. Since in the present case it has been found that it is advantageous to conduct the hydrolysis at temperatures above 100° C., it is desirable to apply a pressure above 1 bar. Therefore, the purified esterified composition is preferably contacted with water at a temperature of 120 to 180° C. and a pressure of 5 to 30 bar.

Saponification conditions may be the same as those of the hydrolysis. However, the temperature may even be lower, e.g. from 60 to 200° C. The pressure may also range from about 1 to 30 bar.

The process according to the present invention may be carried out in batch mode. That would allow the skilled person to apply the optimal conditions for each step separately from any subsequent step. The conditions also include the contact time of the alcohol with the acid composition, the residence time in any crystallizer, and the contact time of the purified esterified composition with water, if such composition is subjected to hydrolysis or saponification. The process according to the invention, however, is preferably conducted as a continuous process. The continuous process may be conducted in a continuous stirred tank reactor or any other continuous reactor. The contact time of the alcohol with the acid composition may for example also be carried out in a plug flow reactor.

Referring to the FIGURE, into a filtration unit A a feed stream 1, comprising an acid composition with 2-formyl-furan-5-carboxylic acid and 2,5-furan-dicarboxylic acid, and a diluent, such as acetic acid, is introduced. The filtration unit results in a mother liquor, comprising the diluent that is withdrawn via a line 3, and the acid composition that is withdrawn from the filtration unit A via a line 2. The acid composition is introduced into a washing unit B, wherein the acid composition is washed with a washing liquid, such as water, supplied via a line 4, to remove impurities, e.g. remaining acetic acid. The washing may be accomplished by stirring the acid composition with the washing liquid at elevated temperature, e.g. 80° C. for a certain period, such as between 0.25 and 1.0 hour. Then the remaining slurry is filtered. It is possible to dry the filter cake, i.e. the acid composition, before treating it further (not shown).

The used washing liquid is discharged via a line 5 and the washed acid composition is passed via a line 6 to an esterification unit C. The acid composition is contacted with an alcohol, e.g. methanol that is introduced via a line 7, optionally in combination with a homogeneous catalyst, e.g. sulphuric acid, which is included in the alcohol. The contact time of the acid composition with the alcohol may be for example 10 hours at a pressure of up to 5 bar and a temperature of about 80° C. Alternatively, the contact is performed at atmospheric reflux conditions (i.e. one bar and e.g. 65° C.) for up to 24 hours. The resulting esterified product is withdrawn via a line 8 and passed into a crystallization unit D. In unit D the compounds from the line 8 are cooled to a temperature of about 20° C. whereby the mono- and diester of 2,5-furan-dicarboxylic acid precipitate. The product obtained is then filtered, yielding a mother liquor, that contains the alcohol, the ester of 2-formyl-furan-5-carboxylic acid and optionally some mono- and diester of 2,5-furan-dicarboxylic acid, that is withdrawn via a line 9, and a purified esterified composition, that mainly comprises 2,5-furan-dicarboxylic acid compounds that is recovered via a line 10.

By means of this line 10 the purified esterified product can be passed to a hydrolysis unit E. In unit E the purified product is dissolved in an aqueous solution of e.g. sodium hydroxide supplied via a line 11 to the unit E, wherein the hydrolysis takes place at reflux conditions. When the hydrolysis is complete, e.g. after two hours, an aliquot of aqueous hydrochloric acid is added via a line 12 to the unit E to neutralise the solution. This results in the precipitation of 2,5-furan-dicarboxylic acid. The precipitate is filtered from the remaining mother liquor and via a line 13 passed to a recrystallization unit F. Water is added to the recrystallization unit F via a line 14 in such quantities that the precipitate from the unit E dissolves completely. This may entail a weight ratio of 2,5-furan-dicarboxylic acid to water of about 1 to 10. The compounds in the recrystallization unit F may be held at reflux conditions, i.e. a temperature of about 100° C. at atmospheric pressure. When all solids are dissolved the obtained solution is allowed to cool to a temperature of about 20° C., resulting in the precipitation of purified 2,5-furan-dicarboxylic acid. The precipitate is filtered and recovered via a line 15. The remaining water phase is discharged via a line 16. The recovered purified 2,5-furan-dicarboxylic acid product may be dried before it is used further.

The invention will be further illustrated by means of the following examples.

EXAMPLE 1

In the following experiments an acid composition was used that was obtained from the oxidation of 5-methoxymethylfurfural in acetic acid in the presence of a catalyst that contained cobalt, manganese and bromide. The acid composition has precipitated and the solid product was filtered to remove the acetic acid. Subsequently, the acid composition was mixed with water, stirred for 30 minutes at 80° C., filtered and dried at ambient temperature at a vacuum of 50 mbar. The acid composition comprised about 1% wt 2-formyl-furan-5-carboxylic acid ("FFCA") and about 3% wt of 2,5-furan-dicarboxylic acid monomethyl ester ("FDCA-ME"), a few ppm of the methyl ester of FFCA ("FFCA-ME"), the balance being 2,5-furan-dicarboxylic acid ("FDCA").

One part by weight of the acid composition was taken up in four parts by weight of methanol, and sulphuric acid was added as esterification catalyst. The mixtures obtained were subjected to different esterification conditions as to pressure, temperature and amount of sulphuric acid. After the esterification reaction had reached equilibrium, the mixtures were allowed to cool to room temperature and left overnight. A precipitate has crystallised. The precipitate was filtered and dried overnight at 50° C. and at 100 mbar. The composition thereof was determined by HPLC. The products contained FFCA, FFCA-ME and 2,5-furan-dicarboxylic acid compounds (FDCA-c), i.e. the acid, the monomethyl ester and the dimethyl ester. The amounts of FFCA and FFCA-ME were determined, the balance being FFDA-c.

The results of the experiments are shown in Table 1 below.

TABLE 1

| Exp. No. | P, bar | T, ° C. | H$_2$SO$_4$, vol % | FFCA, ppmw | FFCA-ME, ppmw |
| --- | --- | --- | --- | --- | --- |
| 1 | 1 | 65 | 1 | 19 | 423 |
| 2 | 8.6 | 140 | 1 | 0 | 56 |
| 3 | 8.8 | 140 | 10 | 0 | 172 |
| 4 | 40.4 | 180 | 1 | 13 | 63 |
| 5 | 5.9 | 120 | 1 | 81 | 429 |

The results show that the esterification and crystallization resulted in a purified esterified product that contained considerably significantly lower amounts of FFCA derivatives than the original acid product.

COMPARATIVE EXPERIMENT 1

An acid product, obtained in a manner similar to the one described in Example 1, was washed with water and the amount FFCA therein was determined. The product was subsequently taken up in water at 90° C. and completely dissolved. The weight ratio of acid product to water was about 1:150. The solution was allowed to cool to 20° C., and a precipitate was formed. The precipitate was filtered off and dried. This precipitate was recrystallized two more times, using this procedure. The yield of solids obtained, based on the weight of the acid product, was determined. The amount of FFCA in the final precipitate was also determined. The results are shown in Table 1C, below.

The recrystallization experiment was repeated with the same acid product as starting material, but in the product was dissolved in acetic acid at 100° C. The weight ratio of acid product to acetic acid was about 1:150. The solution was allowed to cool to 5° C., and a precipitate was formed. The precipitate was filtered off and dried. The yield of solids obtained after three recrystallizations, based on the weight of the acid product, was determined. The amount of FFCA in the final precipitate was also determined. The results are shown in Table 1C, below.

The recrystallization experiment was repeated with the same acid product as starting material, but in the product was dissolved in methanol at 60° C. The weight ratio of acid product to methanol was about 1:26. The solution was allowed to cool to −20° C., and a precipitate was formed. The precipitate was filtered off and dried. The yield of solids obtained after three recrystallizations, based on the weight of the acid product, was determined. The amount of FFCA in the final precipitate was also determined. The results are shown in Table C1, below.

TABLE C1

| Exp. No. | Solvent | FFCA (acid product), ppmw | FFCA (recrystallized), ppmw | Solids Yield, % wt |
| --- | --- | --- | --- | --- |
| C1 | Water | 6244 | 3382 | 53 |
| C2 | Acetic acid | 6244 | 1894 | 60 |
| C3 | Methanol | 6244 | 486 | 15 |

These results show that recrystallization only has a modest effect on the removal of FFCA from the acid product whilst the loss of product is considerable.

EXAMPLE 2

This experiment shows that the esterification reaction can also be carried out in a continuous mode.

In a continuous mode, a feed solution of 1% wt of an FDCA composition containing about 1% wt of FFCA, based on FDCA, in methanol was passed through a 15 ml plug flow reactor at various temperatures and various feed rates, resulting in different residence times. To ensure steady-state conditions, a product sample is not collected until at least three times the volume of the unit has been flushed with the feed. The pressure in the reactor was 100 bar. The feed solution contained a minor amount of sulphuric acid as esterification catalyst. The effect of water was investigated by adding some water to the feed solution. The product contained the esterified product.

Reaction conditions and results are presented in Table 2.

TABLE 2

| Exp. No. | T, ° C. | Water in feed, vol % | time, min | H$_2$SO$_4$, mmol | Conversion, % |
| --- | --- | --- | --- | --- | --- |
| 6 | 240 | 5 | 7.9 | 5 | 99.4 |
| 7 | 240 | 5 | 7.9 | 10 | 94.9 |
| 8 | 220 | 0 | 7.9 | 10 | 95.5 |
| 9 | 220 | 0 | 7.9 | 5 | 95.2 |
| 10 | 180 | 5 | 2.0 | 5 | 36.0 |
| 11 | 180 | 5 | 3.9 | 5 | 85.1 |

The results show that the esterification can effectively be carried out in a continuous process. The product thereof may subsequently be subjected to separation of any derivative of FFCA present therein.

EXAMPLE 3

In a similar way to the process of Example 2, a feed solution of 1% wt of an FDCA acid composition containing 1% wt of FFCA, based on FDCA, in methanol was passed in a continuous mode through a 15 ml plug flow reactor at various temperatures and various feed rates, resulting in different residence times. To ensure steady-state conditions, a product sample is not collected until at least three times the volume of the unit has been flushed with the feed. The product sample is analysed using liquid chromatography. The pressure in the reactor was 100 bar and the temperature was maintained at 200° C. The reactor was loaded with a heterogeneous catalyst as indicated in Table 3. The product contained the esterified product. The residence time in each experiment was 2 min.

The catalysts used were a H-zeolite Y (Cat. No. 1), ultrastable H-zeolite-Y (Cat. No. 2), very ultrastable H-zeolite-Y (Cat. No. 3), dealuminated ultrastable H-zeolite-Y (Cat. No. 4) and SAPO-34 (Cat. No. 5).

Reaction conditions and results are presented in Table 3.

TABLE 3

| Exp. No. | Cat. No. | Conversion, % |
|---|---|---|
| 12 | 1 | 99.9 |
| 13 | 2 | 99.6 |
| 14 | 3 | 84.1 |
| 15 | 4 | 100.0 |
| 16 | 5 | 99.9 |

These results show that the esterification of an FDCA product can very effectively be achieved by means of a zeolitic catalyst. The esterified product may be subjected to separation by means of e.g. crystallization or distillation.

These results show that the esterification can also effectively be conducted using an ion exchange resin as catalyst.

EXAMPLE 5

Two acid products, obtained from two separate oxidations of methoxymethylfurfural over a cobalt/manganese/bromide catalyst, were isolated. The amounts of 2-formyl-furan-5-carboxylic acid and furan-2,5-dicarboxylic acid in both products were determined. One acid product was washed with water in an amount of ten times the weight of the acid product. The other acid product was washed with acetic acid also in an amount of ten times the weight of the acid product.

The acid products were subsequently taken up in methanol (in a 20% slurry) and in a batch reactor maintained at 160° C. and 40 bar for a period of 6 hours. The amounts of the resulting compounds were determined. The washing agent, the composition of the starting materials and the amounts of the resulting compounds are indicated in Table 5, wherein AcOH=acetic acid and FDCA-DME=dimethyl ester of FDCA. The amounts are indicated in molar percentages, based on the starting material and resulting compounds, respectively.

TABLE 5

| | | Start. material | | Resulting compounds[1] | | | | |
|---|---|---|---|---|---|---|---|---|
| Exp. No. | Wash | FDCA | FFCA | FDCA | FDCA-ME | FDCA-DME | FFCA | FFCA-ME |
| 28 | water | 98.8 | 1.2 | 0.9 | 26.3 | 73.1 | 0.1 | 0.7 |
| 29 | AcOH | 98.4 | 1.6 | 4.4 | 18.1 | 74.9 | 0.3 | 1.1 |

[1]Due to analytical experimental actions, the percentages do not exactly add up to 100%.

EXAMPLE 4

Similar to the experiments in Example 3 a series of experiments using a halogenated sulphonated polystyrene-divinylbenzene ion exchange resin, marketed under the trade mark Amberlyst 70, was carried out.

The pressure in the reactor was 100 bar. The temperature varied between 130 and 160° C. The residence time was varied by adjusting the flow rate of the feed solution. The results are indicated in Table 4 below.

TABLE 4

| Exp. No. | T, ° C. | Residence time, min | Conversion, % |
|---|---|---|---|
| 17 | 130 | 1.0 | 51.7 |
| 18 | 130 | 5.0 | 99.7 |
| 19 | 130 | 10.0 | 100.0 |
| 20 | 140 | 2.4 | 93.4 |
| 21 | 140 | 6.9 | 99.4 |
| 22 | 140 | 1.0 | 65.0 |
| 23 | 140 | 5.0 | 99.9 |
| 24 | 140 | 10.0 | 100.0 |
| 25 | 150 | 1.0 | 71.7 |
| 26 | 150 | 5.0 | 100.0 |
| 27 | 160 | 1.0 | 80.2 |

The experiments show that the esterification can suitably be conducted without the use of an additional catalyst.

EXAMPLE 6

In a series of batch experiments the dimethyl ester of 2,5-furan-dicarboxylic acid was taken up in water in the absence or presence of a catalyst. The catalyst was sulphuric acid (catalyst A) or zinc acetate (catalyst B). At various temperatures, pressures and for different contact times the mixture obtained was subjected to hydrolysis. The reaction conditions and the results are shown in Table 6.

TABLE 6

| Exp. No. | T, ° C. | catalyst | Contact time, min | p, bar | FDCA-DME in feed, % wt | Conversion, % |
|---|---|---|---|---|---|---|
| 30 | 100 | 1% wt, A | 300 | 1 | 25 | 24.6 |
| 31 | 120 | 0.25% wt, A | 360 | 20 | 20 | 57.2 |
| 32 | 120 | 1% wt, A | 360 | 20 | 20 | 94.4 |
| 33 | 120 | 1% wt, B | 360 | 20 | 20 | 37.5 |
| 34 | 140 | — | 360 | 20 | 20 | 75.4 |
| 35 | 140 | 1% wt, A | 100 | 20 | 20 | 96.7 |
| 36 | 140 | 1% wt, B | 360 | 20 | 20 | 91.2 |

TABLE 6-continued

| Exp. No. | T, °C. | catalyst | Contact time, min | p, bar | FDCA-DME in feed, % wt | Conversion, % |
|---|---|---|---|---|---|---|
| 37 | 160 | — | 100 | 20 | 20 | 98.2 |
| 38 | 160 | 1% wt, A | 100 | 20 | 20 | 81.2 |
| 39 | 160 | 1% wt, B | 300 | 20 | 20 | 98.5 |
| 40 | 180 | — | 30 | 15 | 25 | 57.6 |

These results show that if the esterified product has been purified, hydrolysis can easily be achieved to recover the acid from FDCA, if such a product is desired.

EXAMPLE 7

An FDCA composition ("Composition A") was taken up in methanol and sulphuric acid in a closed vessel. The weight ratio of the FDCA composition to methanol was 1:4. The resulting mixture was subjected to esterification at 80° C. for about 12 hours at autogenous pressure. A precipitate was formed, which was filtered off. The filter cake was redissolved in methanol at 60° C. and recrystallized by cooling to 25° C. The thus recrystallized product containing mainly FDCA-DME was recovered by filtration and dried ("Composition B").

Composition B was mixed with an aqueous sodium hydroxide solution; the equivalent ratio of sodium hydroxide to the dimethyl ester of FDCA was 2.41. The diester was saponified to the disodium salt by heating the mixture at about 80° C. at about atmospheric pressure. The amount of water was sufficient to solubilise the disodium salt completely.

The disodium salt was neutralised by adding a small excess of sulphuric acid whereby freed FDCA precipitated. The precipitated FDCA was recovered by filtration, and washed with water. The washed FDCA product was removed from the filter and taken up in water at 150° C. and at 5 bar to fully dissolve the FDCA product. The solution obtained was cooled to ambient temperature, whilst recrystallized FDCA precipitated. This recrystallized FDCA product was obtained by filtration and subsequent drying in vacuo at 70° C. ("Composition C"). The yield of Composition C was about 65 mole %, based on Composition A.

The components of Compositions A, B and C are shown in Table 7.

TABLE 7

| Composition | FFCA, ppmw | FFCA-ME, ppmw | FDCA, % wt | FDCA-ME, ppmw | FDCA-DME, % wt |
|---|---|---|---|---|---|
| A | 8751 | 21 | 98.0 | 10,616 | — |
| B | 0 | 18 | — | 3,149 | 99.7 |
| C | 0 | 0 | 100.0 | 37 | — |

The results show that the sequence of esterification of an FDCA product with subsequent recrystallization and saponification leads to a satisfactory yield of pure FDCA product.

The invention claimed is:

1. A process for purifying an acid composition comprising 2-formyl-furan-5-carboxylic acid and 2,5-furandicarboxylic acid, which process comprises the steps of:
   contacting the acid composition with an alcohol to obtain an esterified composition;
   separating the ester of 2-formyl-furan-5-carboxylic acid from the esterified composition to obtain a purified esterified product; and
   contacting the purified esterified composition with water for saponification or hydrolysis, to obtain a product composition, comprising 2,5-furandicarboxylic acid and a reduced amount of 2-formyl-furan-5-carboxylic acid.

2. The process according to claim 1, wherein the acid composition originates from the oxidation of 5-alkoxymethylfurfural, 5-hydroxymethylfurfural or a mixture thereof.

3. The process according to claim 1, wherein the acid composition comprises from 0.1 to 4.0% wt of 2-formyl-furan-5-carboxylic acid, based on the weight of the acid composition.

4. The process according to claim 1, wherein the acid composition is contacted with a mono-alcohol.

5. The process according to claim 4, wherein the mono-alcohol is an alkanol having from 1 to 8 carbon atoms.

6. The process according to claim 1, wherein the alcohol is present in a molar excess of the acid composition.

7. The process according to claim 1, wherein the acid composition is contacted with an alcohol in the presence of an esterification catalyst.

8. The process according to claim 1, wherein the acid composition is contacted with an alcohol in the absence of an esterification catalyst.

9. The process according to claim 7, wherein the esterification catalyst is an acid catalyst, the acid catalyst being selected from the group consisting of mineral inorganic acids, zeolites, ion exchange resins and mixtures thereof.

10. The process according to claim 1, wherein the acid composition is contacted with an alcohol at a temperature of 60 to 250° C. and a pressure of 1 to 100 bar.

11. The process according to claim 1, wherein the esterified composition is subjected to crystallization and/or distillation.

12. The process according to claim 11, wherein the esterified composition is allowed to crystallize by cooling the esterified composition to a temperature of −30 to 40° C.

13. The process according to claim 12, wherein the purified esterified composition is allowed to crystallize by cooling the esterified composition to a temperature of −10 to 30° C.

14. The process according to claim 1, wherein the purified esterified composition is contacted with water in the presence of a hydrolysis catalyst.

15. The process according to claim 1, wherein the purified esterified composition is contacted with water in the absence of a hydrolysis catalyst.

16. The process according to claim 1, wherein the purified esterified composition is contacted with water at a temperature of 120 to 180° C. and a pressure of 5 to 30 bar.

17. The process according to claim 1, which is conducted as a continuous process.

18. The process according to claim 4, wherein the mono-alcohol is an alkanol having from 1 to 8 carbon atoms.

19. The process according to claim 1, wherein the alcohol is present in a molar excess of the acid composition, the molar ratio between alcohol and the acid composition being from 5:1 to 100:1.

20. The process according to claim 1, wherein the acid composition is contacted with an alcohol at a temperature of 70 to 200° C. and a pressure of 1 to 70 bar.

21. The process according to claim 18, wherein the alkanol is ethanol or methanol.

* * * * *